US011447815B2

(12) United States Patent
Chen et al.

(10) Patent No.: US 11,447,815 B2
(45) Date of Patent: Sep. 20, 2022

(54) METHODS FOR THE ANALYSIS OF PROXIMITY BINDING ASSAY DATA

(71) Applicant: LIFE TECHNOLOGIES CORPORATION, Carlsbad, CA (US)

(72) Inventors: Shiaw-Min Chen, Fremont, CA (US); David W. Ruff, San Francisco, CA (US); Harrison Leong, San Francisco, CA (US)

(73) Assignee: Life Technologies Corporation, Carlsbad, CA (US)

( * ) Notice: Subject to any disclaimer, the term of this patent is extended or adjusted under 35 U.S.C. 154(b) by 944 days.

(21) Appl. No.: 16/228,304

(22) Filed: Dec. 20, 2018

(65) Prior Publication Data

US 2019/0241942 A1 Aug. 8, 2019

Related U.S. Application Data

(62) Division of application No. 12/851,532, filed on Aug. 5, 2010, now Pat. No. 10,208,335.

(60) Provisional application No. 61/231,649, filed on Aug. 5, 2009.

(51) Int. Cl.
*C12Q 1/6844* (2018.01)
*G16B 25/00* (2019.01)
*G16B 40/00* (2019.01)
*G16B 25/20* (2019.01)
*G16B 40/10* (2019.01)

(52) U.S. Cl.
CPC .......... *C12Q 1/6844* (2013.01); *G16B 25/00* (2019.02); *G16B 25/20* (2019.02); *G16B 40/00* (2019.02); *G16B 40/10* (2019.02)

(58) Field of Classification Search
None
See application file for complete search history.

(56) References Cited

U.S. PATENT DOCUMENTS

| 4,683,202 | A | 7/1987 | Mullis |
| 5,494,810 | A | 2/1996 | Barany et al. |
| 5,538,848 | A | 7/1996 | Livak et al. |
| 5,830,711 | A | 11/1998 | Barany et al. |
| 5,925,517 | A | 7/1999 | Tyagi et al. |
| 5,942,432 | A | 8/1999 | Smith |
| 6,054,564 | A | 4/2000 | Barany et al. |
| 6,103,476 | A | 8/2000 | Tyagi et al. |
| 6,150,097 | A | 11/2000 | Tyagi et al. |
| 6,235,504 | B1 | 5/2001 | Zhang et al. |
| 6,355,421 | B1 | 3/2002 | Coull et al. |
| 6,383,752 | B1 | 5/2002 | Agrawal et al. |
| 6,387,621 | B1 | 5/2002 | Wittwer |
| 6,485,901 | B1 | 11/2002 | Gildea et al. |
| 6,548,250 | B1 | 4/2003 | Sorge |
| 6,589,250 | B2 | 7/2003 | Schendel |
| 6,589,743 | B2 | 7/2003 | Sorge |
| 6,590,091 | B2 | 7/2003 | Albagli et al. |
| 6,593,091 | B2 | 7/2003 | Keys et al. |
| 6,596,490 | B2 | 7/2003 | Dattagupta |
| 7,125,691 | B2 | 10/2006 | Sagner et al. |
| 7,228,237 | B2 | 6/2007 | Woo et al. |
| 8,099,243 | B2 | 1/2012 | Shain et al. |
| 10,208,335 | B2 | 2/2019 | Chen et al. |
| 2006/0024690 | A1 | 2/2006 | Kao et al. |

FOREIGN PATENT DOCUMENTS

WO 99/021881 A1 5/1999

OTHER PUBLICATIONS

Office Action issued in European Patent Application No. 10 807 190.3 dated Oct. 23, 2018, 9 pages.
International Search Report and Written Opinion for International Application No. PCT/US10/44615 dated Sep. 23, 2010, 11 pages.
Broude, Natalia E., "Stem-loop oligonucleotides: a robust tool for molecular biology and biotechnology," Trends in Biotechnology, vol. 20, No. 6, Jun. 2002, pp. 249-256.
Kubista, Mikael et al., "Light-up probe based real-time Q-PCR," Proceedings of SPIE, vol. 4264, 2001, pp. 53-58.
Huang, Weidong et al., "Fluorescence Characteristics of Site-Specific and Stereochemically Distinct Bezo[a]pyrene Diol Epoxide-DNA Adducts as Probes of Adduct Conformation," Chem. Res. Toxicol., vol. 15, No. 2, 2002, pp. 118-126.
Isacsson, J. et al., "Rapid and specific detection of PCR products using light-up probes," Molecular and Cellular Probes, vol. 14, 2000, pp. 321-328.
Maxwell, Dustin J. et al., "Self-Assembled Nanoparticle Probes for Recognition and Detection of Biomolecules," J. of Am. Chem. Soc., vol. 124, 2002, pp. 9606-9612.
Mhlanga, Musa M. et al., "Using Molecular Beacons to Detect Single-Nucleotide Polymorphisms with Real-Time PCR," Methods, vol. 25, 2001, pp. 463-471.
Riccelli, Peter V. et al., "Melting studies of dangling-ended DNA hairpins: effects of end length, loop sequence and biotinylation of loop bases," Nucleic Acids Research, vol. 30, No. 18, 2002, pp. 4088-4093.
Solinas, Antonio et al., "Duplex Scorpion primers in SNP analysis and FRET applications," Nucleic Acids Research, vol. 29, No. 20, E96, 2001, 9 pages.
Svanvik, Nicke et al., "Light-up Probes: Thiazole Orange-Conjugated Peptide Nucleic Acid for Detection of Target Nucleic Acid in Homogenous Solution," Anal Biochem., vol. 281, 2000, pp. 26-35.

(Continued)

*Primary Examiner* — Michael L Borin
(74) *Attorney, Agent, or Firm* — Mauriel Kapouytian Woods LLP; Michael Mauriel

(57) ABSTRACT

Various embodiments of methods for analyzing proximity binding assay (PBA) data are disclosed. Proximity binding assays as a class of analyses offer the advantages of the sensitivity and specificity of biorecognition binding, along with the exponential signal amplification offered by a variety of oligonucleotide amplification reactions, such as the polymerase chain reaction (PCR). However, as various proximity binding assays have reaction kinetics governed by an additional step of the binding of a biorecognition probe (BRP) with a target molecule, there is a need for methods for the analysis of PBA data that are particularly suited to the unique characteristics of such data.

14 Claims, 13 Drawing Sheets

(56) References Cited

OTHER PUBLICATIONS

Tsourkas, Andrew et al., "Structure-function relationships of shared-stem and conventional molecular beacons," Nucleic Acids Research, vol. 30, No. 19, 2002, pp. 4208-4215.
Tyagi, Sanjay et al., "Molecular Beacons: Probes that Fluoresce upon Hybridization," Nature Biotechnology, vol. 14, 1996, pp. 303-308.
Yu, C.J. et al., "Electronic Detection of Single-Base Mismatches in DNA with Ferrocene-Modified Probes," J. Am. Chem. Soc., vol. 123, No. 45, 2001, pp. 11155-11161.
Whitcombe, David et al., "Detection of PCR products using self-probing amplicons and fluorescence," Nature Biotechnology, vol. 17, 1999, pp. 804-807.
Wolffs, Petra et al., "PNA-Based Light-Up Probes for Real-Time Detection of Sequence-Specific PCR Products," BioTechniques, vol. 31, 2001, pp. 766-771.
Zhang, Yong-You et al., "Hairpin Probes for Real-time Assay of Restriction Endonucleases," Natl. Acad. Sci USA, vol. 97, No. 25, 2000, pp. 329-332.
Fredriksson, Simon et al., "Protein detection using proximity-dependent DNA ligation assays," Nature Biotechnology, vol. 20, 2002, pp. 473-477.
Extended European Search Report for European Application No. 10807190.3 dated Jul. 13, 2015, 7 Pages.
LightCycler480 Instrument Operator's Manual—Software Version 1.5, Roche Diagnostics GmbH, 2008, pp. 1-395.

METHODS FOR THE ANALYSIS OF PROXIMITY BINDING ASSAY DATA

CROSS REFERENCE TO RELATED APPLICATIONS

This application is a divisional application of U.S. application Ser. No. 12/851,532 filed on Aug. 5, 2010, which claims priority to U.S. Provisional Application No. 61/231,649 filed on Aug. 5, 2009. The entire contents of these applications are hereby incorporated herein by reference.

FIELD

The field of disclosure of relates to methods for analyzing proximity binding assay (PBA) data, which overcome the shortcomings of traditional methods for the analysis of amplification data for oligonucleotides for such assays.

BACKGROUND

For numerous types of bioanalysis, the sensitive quantitation of a biomolecule at low levels in a sample is highly desirable. For example, it may be desirable to monitor the dynamic expression levels of an intact, post-translationally modified protein in a particular cell or tissue sample or samples. In many cases, the amount of sample of interest; for example, the number of cells or mass of tissue, may be very small. Additionally, the number of copies of the target protein of interest may be very low. In such cases, it may be desirable to assay a protein concentration in sub-femtormole concentrations.

Currently, proximity binding assays as a class of analyses offer the advantages of the sensitivity and specificity of biorecognition binding, along with the exponential signal amplification offered by a variety of oligonucleotide amplification reactions, such as the polymerase chain reaction (PCR).

However, the combination of a binding event, followed by an oligonucleotide amplification reaction event produces data with characteristics requiring specialized analysis methods. Such methods should be readily adapted to the broad class of proximity binding assays, and should provide the user with results presented in readily useful form and format. Accordingly, there is a need in the art for methods for the analysis of proximity binding assay (PBA) data.

DETAILED DESCRIPTION

What is disclosed herein are various embodiments of methods for analyzing proximity binding assay (PBA) data. Proximity binding assays as a class of analyses offer the advantages of the sensitivity and specificity of biorecognition binding, along with the exponential signal amplification offered by a variety of oligonucleotide amplification reactions, such as, but not limited by, the polymerase chain reaction (PCR). However, unlike the class of oligonucleotide amplification reactions, the class of proximity binding assays has reaction kinetics governed by an additional step of the binding of a biorecognition probe (BRP) with a target molecule, as well be discussed in more detail subsequently. Accordingly, various embodiments of proximity binding assays may require methods for the analysis of PBA data that are particularly suited to the unique characteristics of such data.

Figure 1:
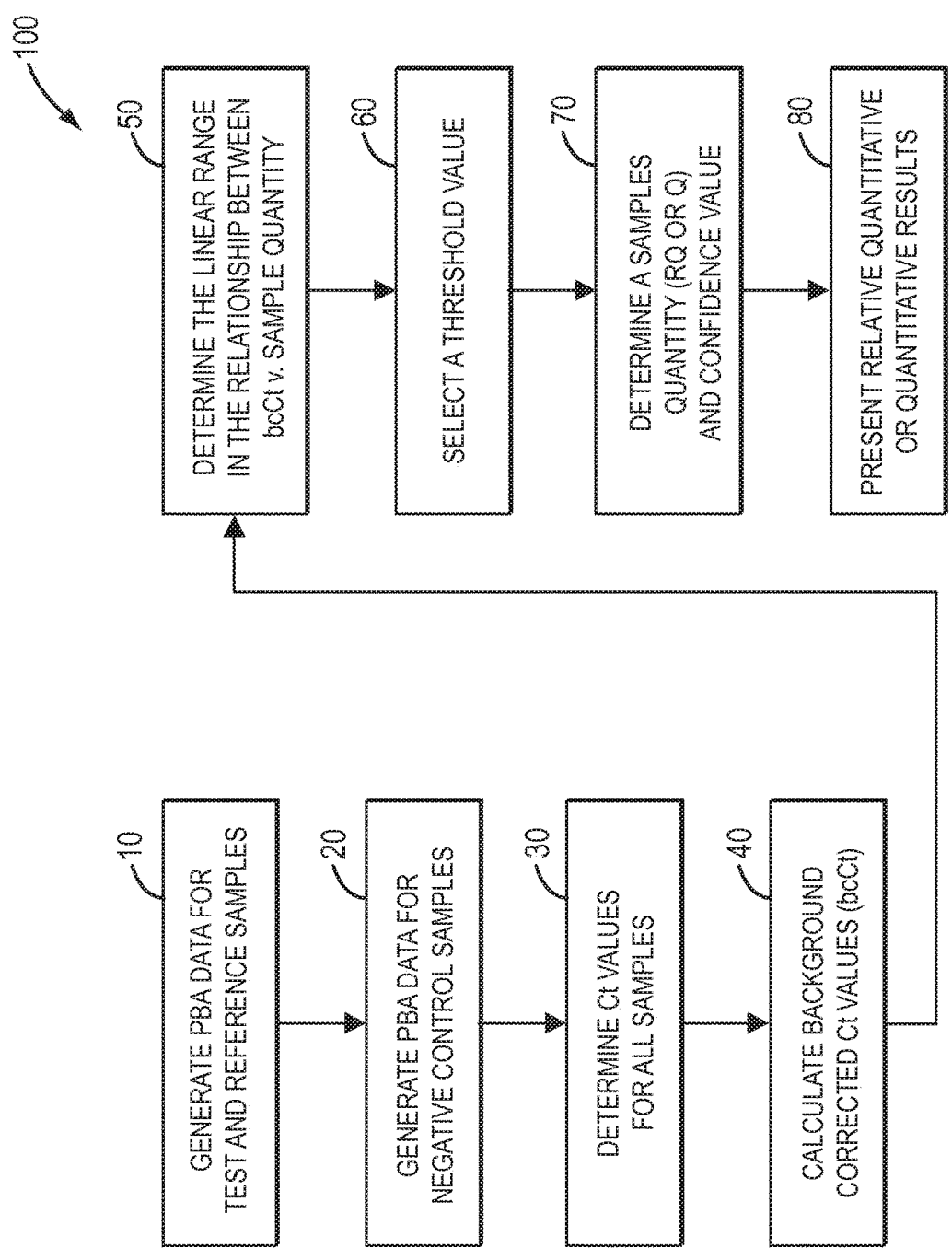
FIG. 1 is a flow chart that depicts various embodiments of methods for the analysis of proximity binding assay (PBA) data.
Figure 2A:
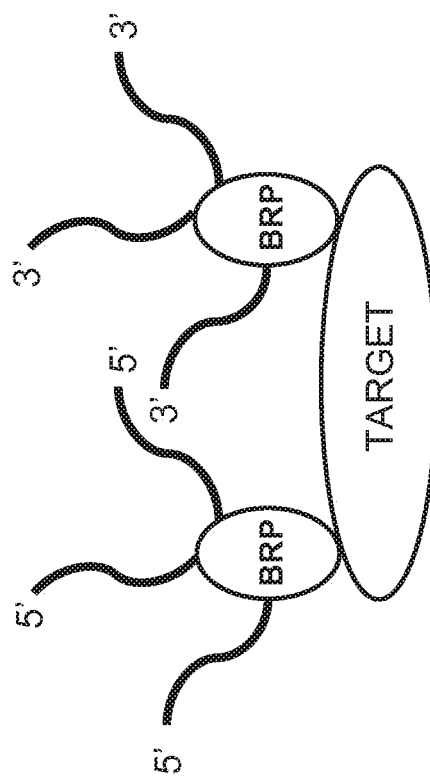
FIG. 2A-FIG. 2D depict various embodiments of a proximity binding assay.
Figure 2B:
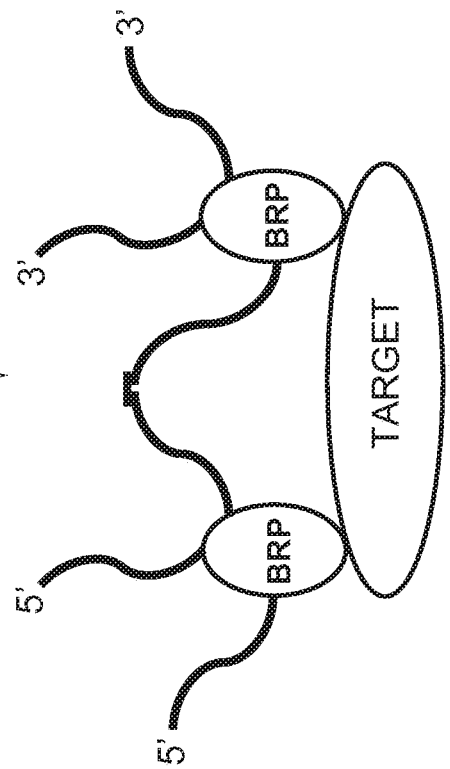
Figure 2C:
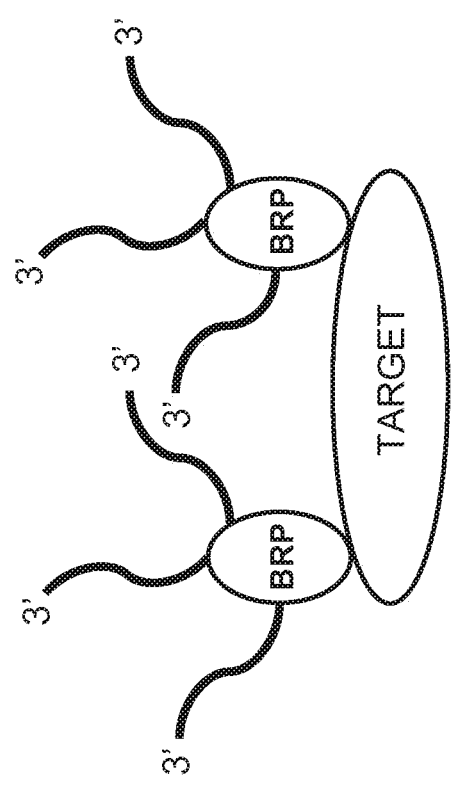

Various embodiments of methods for the analysis of PBA data may be performed using various embodiments of method 100 of FIG. 1. As depicted in FIG. 2A-FIG. 2C, proximity binding assays may be characterized by a biorecognition binding event, as depicted in FIG. 2A, in which a biorecognition probe (BRP) binds to a target biomolecule. For bioanalysis, examples of biorecognition binding may include, but are not limited by oligonucleotide-oligonucleotide, protein-protein, ligand-receptor, antigen-antibody, lectin-polysaccharide, aptamer-protein, enzyme-substrate, and cofactor-protein. According to various embodiments of proximity binding assays, a BRP may enable signal amplification in order to provide for the detection of the target molecule.

Figure 2D:
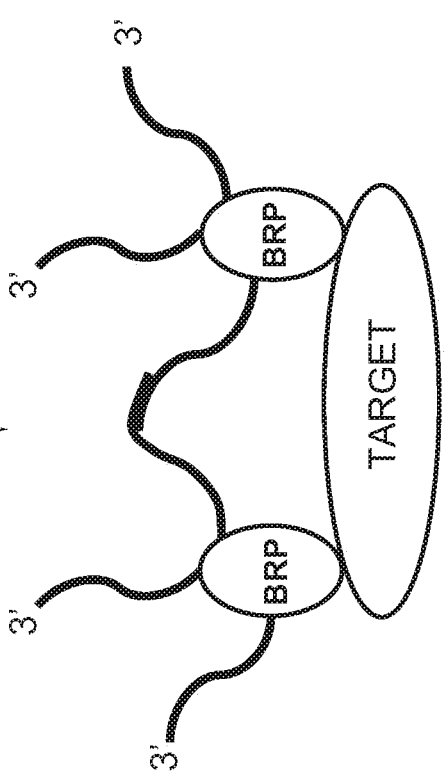

In FIG. 2A-FIG. 2D, various embodiments of BRPs modified with oligonucleotide sequences are shown. According to various embodiments, as shown in FIG. 2A, BRPs may be prepared so that strands in proximity to one another after the binding of the BRPs to a target are of opposite orientation. For various embodiments of BRPs, as shown in FIG. 2B, one population of BRP may have 3' strands of an oligonucleotide sequence coupled to it, while a second population of BRP may have 5' strands of an oligonucleotide sequences coupled to it, so that the strands in proximity to one another after binding are of the same orientation. For various embodiments of a PBA as shown in FIG. 2A, the BRPs may be designed so that at least the free distal end sequences are complementary, so that the binding of complementary sequences produces a target for extension, as shown in FIG. 2C. For various embodiments of proximity binding assays, with the addition of a splint oligonucleotide in the presence of a ligase enzyme, the proximal 3' and 5' ends may be ligated, as shown in FIG. 2D, forming a targets for ligation. For either example, as depicted in FIG. 2C and FIG. 2D, after a target for amplification is formed, and with the addition of amplification reaction components, followed by thermocycling in a thermal cycling system, sequence detection data may be generated. Other methods for detecting oligonucleotides brought into proximity for various embodiments of proximity binding assays include, for example, but not limited by, restriction digestion, and polymerase extension.

According to various embodiments, the term. "amplifying". "amplification" and related terms may refer to any process that increases the amount of a desired nucleic acid. Any of a variety of known amplification procedures may be employed in the present teachings, including PCR (see for example U.S. Pat. No. 4,683,202), as well as any of a variety of ligation-mediated approaches, including LOR and LCR (see for example U.S. Pat. Nos. 5,494,810, 5,830,711, 6,054, 564). Some other amplification procedures include isothermal approaches such as rolling circle amplification and helicase-dependent amplification. One of skill in art will readily appreciate a variety of possible amplification procedures applicable in the context of the present teachings. For example, in some embodiments, the amplification may comprise a PCR comprising a real-time detection, using for example a labeling probe.

The term "labeling probe" generally, according to various embodiments, refers to a molecule used in an amplification reaction, typically for quantitative or real-time PCR analysis, as well as end-point analysis. Such labeling probes may be used to monitor the amplification of the target polynucleotide. In some embodiments, oligonucleotide probes present in an amplification reaction are suitable for monitoring the amount of amplicon(s) produced as a function of time. Such oligonucleotide probes include, but are not limited to, the 5'-exonuclease assay TaqMan® probes described herein (see also U.S. Pat. No. 5,538,848), various stem-loop molecular beacons (see e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355, 421 and 6,593,091), linear PNA beacons (see, e.g., Kubista et al., 2001, SPIE 4264:53-58), non-FRET probes (see, e.g., U.S. Pat. No. 6,150,097), Sunrise®/Amplifluor® probes (U.S. Pat. No. 6,548,250), stem-loop and duplex Scorpion™ probes (Solinas et al., 2001. Nucleic Acids Research 29:E96 and U.S. Pat. No. 6,689,743), bulge loop probes (U.S. Pat. No. 6,590,091), pseudo knot probes (U.S. Pat. No. 6,589, 250), cyclicons (U.S. Pat. No. 6,383,752), MOB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 26:463-471; Whitcombe et al., 1999. Nature Biotechnology, 17:804-807; Iaaceson et al., 2000, Molecular Cell Probes, 14:321-328; Svanvik et al., 2000, Anal Biochem. 281:26-35; Wolffs et al., 2001, Biotechniques 766:769-771; Tsourkas et al., 2002, Nucleic Acids Research, 30:4208.4215; Riccelli et al., 2002. Nucleic Acids Research 30:4088-4093; Zhang et al., 2002 Shanghai, 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155.11161. Labeling probes can also comprise black hole quenchers (Biosearch), Iowa Black (IDT), QSY quencher (Molecular Probes), and Dabsyl and Dabcel sulfonate/carboxylate Quenchers (Epoch). Labeling probes can also comprise two probes, wherein for example a fluorophore is on one probe, and a quencher on the other, wherein hybridization of the two probes together on a target quenches the signal, or wherein hybridization on target alters the signal signature via a change in fluorescence. Labeling probes can also comprise sulfonate derivatives of fluorescenin dyes with a sulfonic acid group instead of the carboxylate group, phosphoramidite forms of fluorescein, phosphoramidite forms of CY 5 (available for example from Amersham). In some embodiments, interchelating labels are used such as ethidium bromide, SYBR® Green I (Molecular Probes), and PicoGreen® (Molecular Probes), thereby allowing visualization in real-time, or end point, of an amplification product in the absence of a labeling probe.

According to various embodiments of proximity binding assays, the target may be a protein. For various embodiments of a proximity binding assay for proteins, a BRP may be directed to a polypeptide primary, secondary, or tertiary structure, such as an aptamer or antibody, or may be directed to a group such as any of a variety of chemical resulting from the in vivo or in vitro modification of a polypeptide structure.

Figure 3:
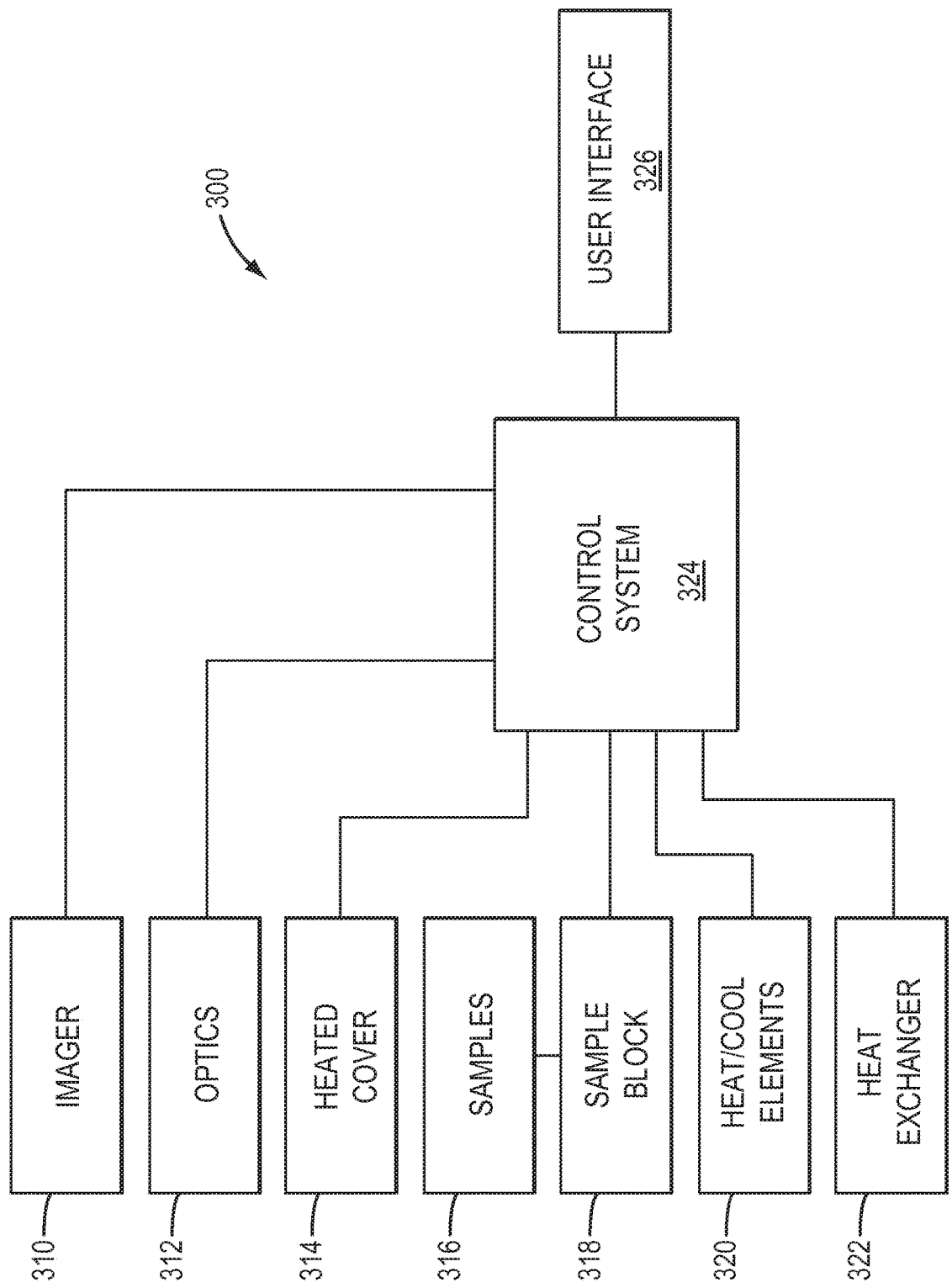
FIG. 3 depicts various embodiments of an apparatus useful in the generation of PBA data.

According to various embodiments of a thermal cycler instrument 300, as shown in FIG. 3, a thermal cycling instrument may include a heated cover 314 that is placed over a plurality of samples 810 contained in a sample support device. In various embodiments, a sample support device may be a glass or plastic substrate material having a plurality of sample regions, which sample regions may have a cover between the sample regions and heated cover 314. Some examples of a sample support device may include, but are not limited by, sample tubes or vials, a multi-well plate, such as a standard microtiter plate (i.e. for example, but not limited by, a 96-well, a 384-well plate, 1536-well plate, etc), a microcard, or a substantially planar support, such as a glass or plastic slide. The sample regions in various embodiments of a sample support device may include depressions, indentations, ridges, and combinations thereof, patterned in regular or irregular arrays formed on the surface of the substrate. Various embodiments of a thermal cycler instrument 800 may include a thermal block assembly, which may include a sample block 318, as well as elements for heating and cooling 320, and a heat exchanger 322.

Figure 4:
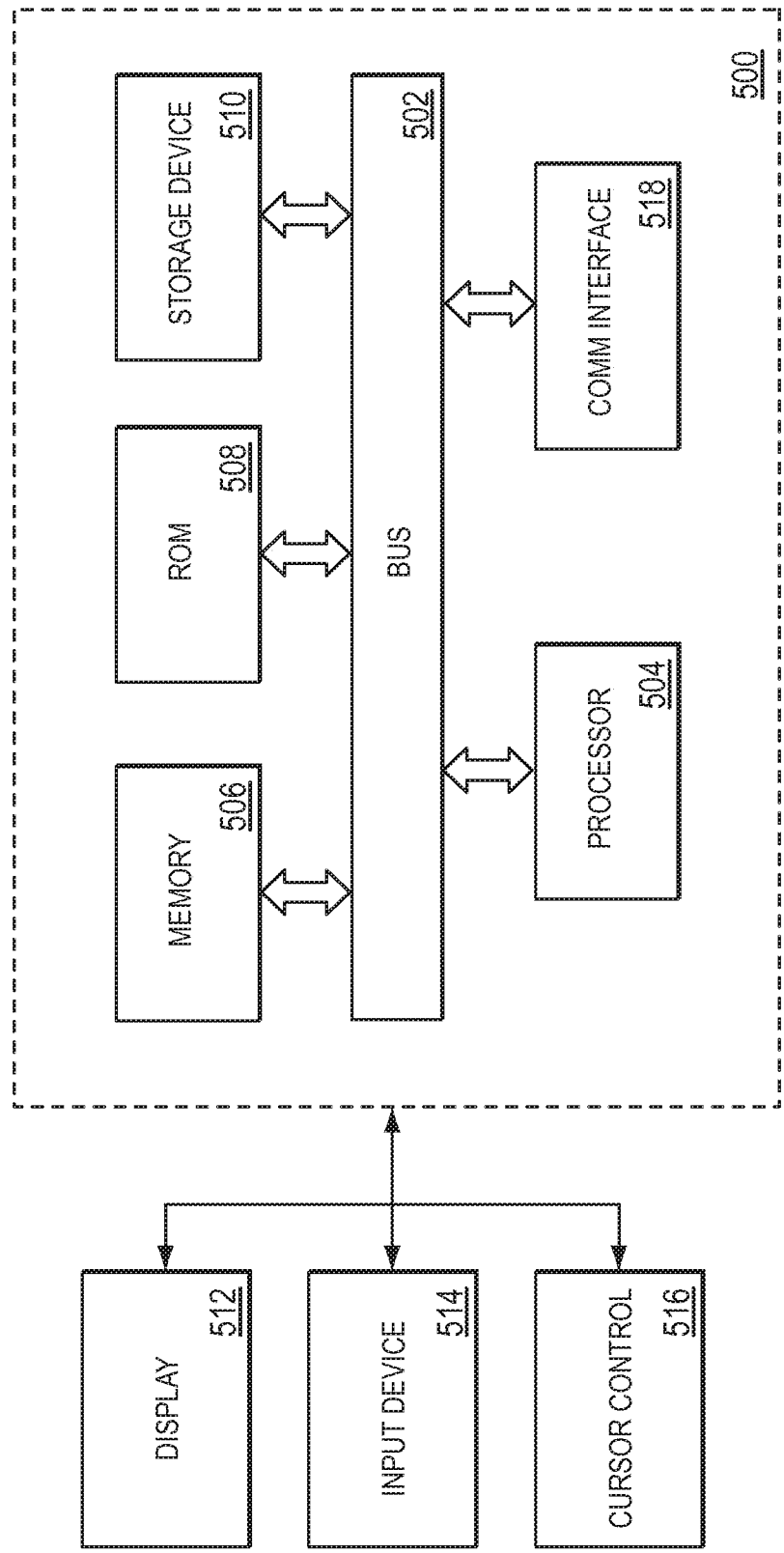
FIG. 4 is a block diagram that illustrates a computer system according to various embodiments upon which embodiments of methods for the analysis of PBA data may be implemented.

Additionally, various embodiments of a thermal cycling system 800 may have a detection system. A detection system may have an illumination source that emits electromagnetic energy (not shown), a detector or imager 810, for receiving electromagnetic energy from samples 316 in sample support device, and optics 312, which may be located between the illumination source and detector or imager 810. For various embodiments of a thermal cycler instrument 300, a control system 824 may be used to control, for example, but not limited by, the functions of the detection, heated cover, and thermal block assembly. The control system 324 may be accessible to an end user through user interface 326 of a thermal cycler instrument 300. In addition to a user interface system 826, a computer system 500, as depicted in FIG. 4 may serve as to provide control of various functions of a thermal cycler instrument. Additionally, computer system 500 may provide data processing, display and report preparation functions. All such instrument control functions may be dedicated locally to the thermal cycler instrument, or computer system 500 may provide remote control of part or all of the control, analysis, and reporting functions, as will be discussed in more detail subsequently.

FIG. 4 is a block diagram that illustrates a computer system 500, according to various embodiments, upon which embodiments of methods for the analysis of PBA data may be implemented. Computer system 500 includes a bus 602 or other communication mechanism for communicating information, and a processor 504 coupled with bus 502 for processing information. Computer system 500 also includes a memory 506, which can be a random access memory (RAM) or other dynamic storage device, coupled to bus 502, and instructions to be executed by processor 504. Memory 506 also may be used for storing temporary variables or other intermediate information during execution of instructions to be executed by processor 504. Computer system 500 further includes a read only memory (ROM) 508 or other static storage device coupled to bus 502 for storing static information and instructions for processor 504. A storage device 610, such as a magnetic disk or optical disk, is provided and coupled to bus 502 for storing information and instructions.

Computer system 500 may be coupled via bus 502 to a display 512, such as a cathode ray tube (CRT) or liquid crystal display (LCD), for displaying information to a computer user. An input device 514, including alphanumeric and other keys, is coupled to bus 502 for communicating information and command selections to processor 504. Another type of user input device is cursor control 5186, such as a mouse, a trackball or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane. A computer system 600 may provide the determination of a result for a set of sample data, and a level of confidence for a result. Consistent with certain implementations of the invention, such results and confidence values are provided by computer system 500 in response to processor 504 executing one or more sequences of one or more instructions contained in memory 506. Such instructions may be read into memory 506 from another computer-readable medium, such as storage device 610. Execution of the sequences of instructions contained in memory 506 causes processor 504 to perform the process states described herein. Alternatively hard-wired circuitry may be used in place of or in combination with software instructions to implement the invention. Thus implementations of the invention are not limited to any specific combination of hardware circuitry and software.

The term "computer-readable medium" as used herein refers to any media that participates in providing instructions to processor 504 for execution. Such a medium may take many forms, including but not limited to, non-volatile media, volatile media, and transmission media. Non-volatile media includes, for example, optical or magnetic disks, such as storage device 610. Volatile media includes dynamic memory, such as memory 506. Transmission media includes coaxial cables, copper wire, and fiber optics, including the wires that comprise bus 502. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 504 for execution. For example, the instructions may initially be carried on magnetic disk of a remote computer. The remote computer can load the instructions into its dynamic memory and send the instructions over a telephone line using a modem. A modem local to computer system 500 can receive the data on the telephone line and use an infra-red transmitter to convert the data to an infra-red signal. An infra-red detector coupled to bus 502 can receive the data carried in the infra-red signal and place the data on bus 502. Bus 502 carries the data to memory 606, from which processor 604 retrieves and executes the instructions. The instructions received by memory 506 may optionally be stored on storage device 510 either before or after execution by processor 504.

Further, it should be appreciated that a computer 500 may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

In various embodiments of steps 10 and 20 of method 100 of FIG. 1, for various embodiments of PBA data for protein analysis, test, reference and negative control samples may be run, and the data may be collected and analyzed using computer system 500. For example, according to various embodiments of a proximity binding assay, an end user may wish to assess the up or down regulation of a protein or proteins in a cell line. For various embodiments of such assays, test samples of a cell line subjected to various conditions may be run. For various embodiments of bioanalyses assessing the up or down regulation of a protein or proteins in a cell line, the determination may be relative quantitation (RQ), in which a reference may be a cell line control may have a target protein or proteins in a defined state. For various embodiments of bioanalyses assessing the up or down regulation of a protein or proteins in a cell line, the determination may be quantitative, in which a reference is a set of calibrators of known concentration.

For various embodiments of proximity binding assays utilizing ligated amplicons, as shown for FIG. 2, there is a finite probability that amplicon formation may occur in the absence of target, creating background signal thereby. Additionally, for various embodiments of BRPs, binding may be influenced by variables in a reaction matrix. For example, antigen-antibody binding is known to be influenced by such matrix effects. For at least these reasons, for various embodiments of methods for the analysis of PBA data, as indicated in step 20 of method 100 of FIG. 1, a negative control may be run, in which a target molecule is absent, and the control is designed to compensate for background and matrix effects. According to various embodiments of method 100, the protocols for generating data for test, reference, and negative control samples are not constrained with respect to the manner in which the data may be generated. For example, but not limited by, for various embodiments, samples as indicated in steps 10 and 20 of method 100 may be run in the same run on the same instrument on the same day, while for other embodiments of method 100, test, reference, and negative control samples may be run on different days and on different instruments.

According to various embodiments of methods for the analysis of PBA data, as depicted in step 30 of method 100 of FIG. 1, the determination of threshold cycle or Ct may be done. As one of ordinary skill in the art is apprised, the Ct is the cycle number for an oligonucleotide amplification reaction at which the fluorescence generated for a sample exceeds a defined threshold. The threshold cycle, then, is defined as the cycle number of an oligonucleotide amplification reaction at which a sufficient number of amplicons have accumulated to provide for analytical detection above noise. According to various embodiments of step 30 of method 100, a variety of approaches may be taken to determine a Ct value. For example, U.S. Pat. No. 7,228,237 to Woo et al. discloses various embodiments for automatic threshold setting for oligonucleotide amplification reactions, and is incorporated in its entirety by reference herein.

Figure 5:
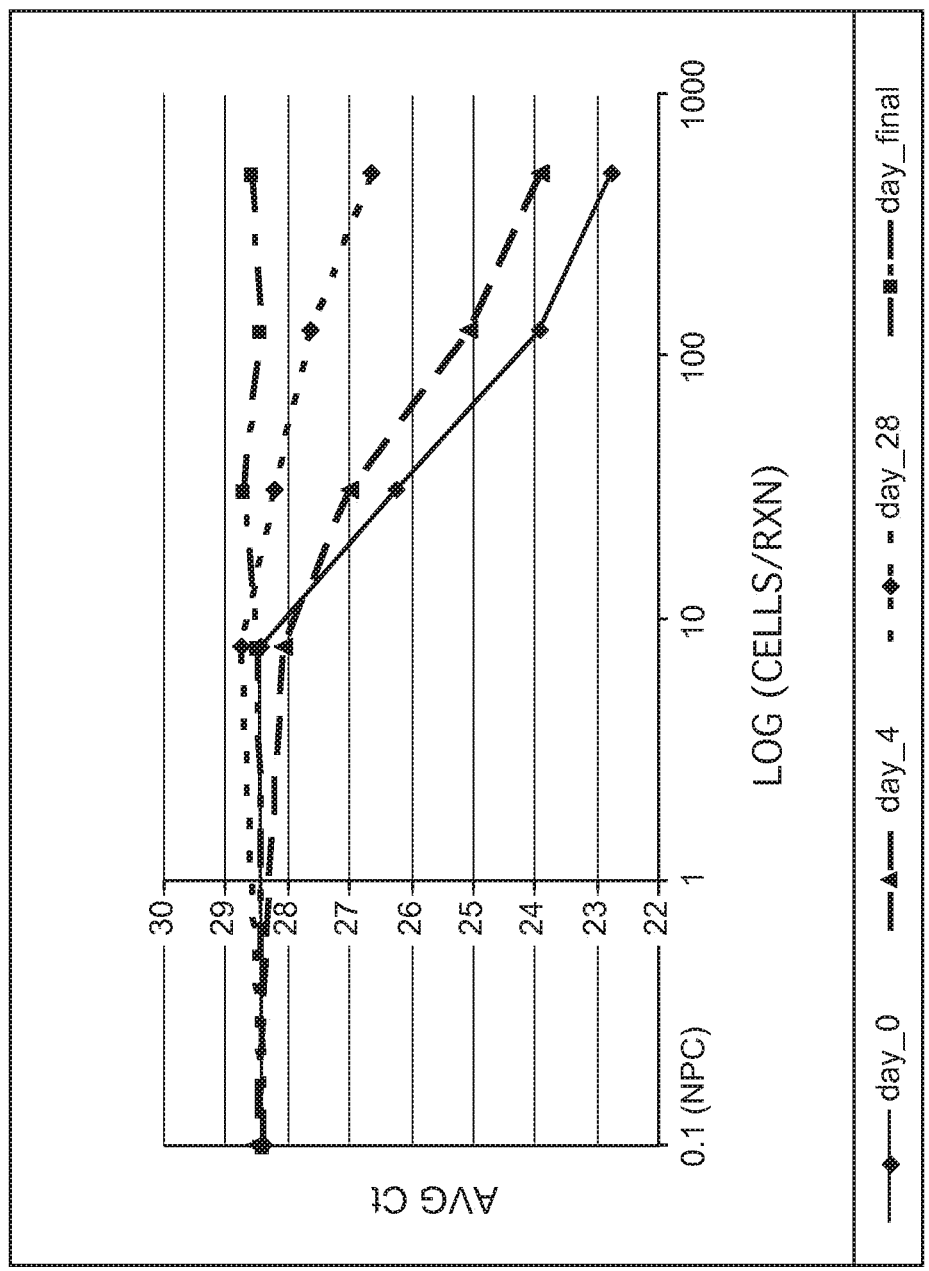
FIG. 5 depicts exemplary graphs of Ct values as a function of log of quantity of test sample for an exemplary proximity binding assay.
Figure 6:
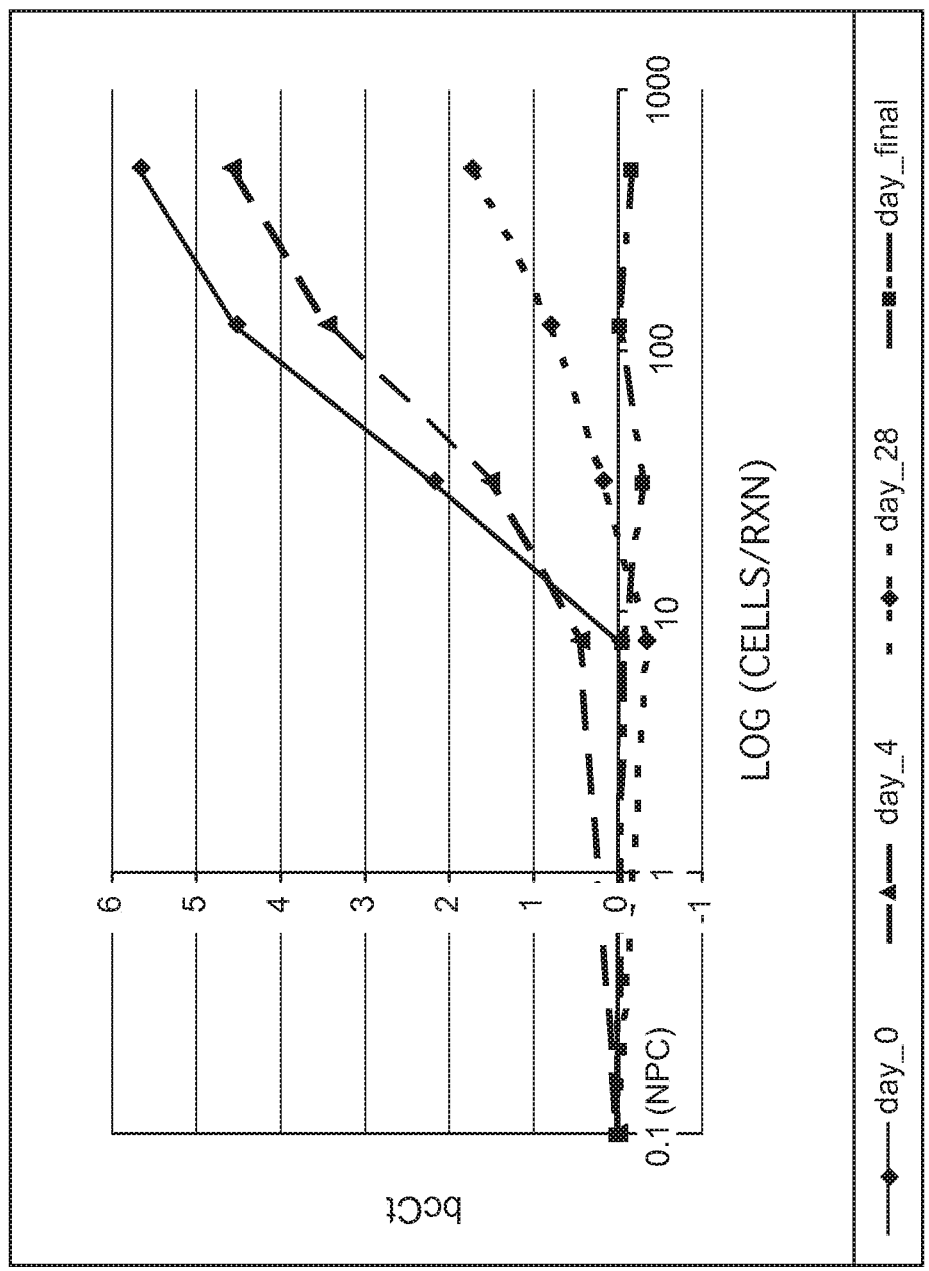
FIG. 6 depicts the exemplary graphs of FIG. 5 that have been corrected for background according to various embodiments of methods for the analysis of PBA data.

In FIG. 5, a plot of the Ct values as a function of sample quantity for PBA data generated for the analysis of the protein OCT3/4 in a NTERA-2 cell line is shown. According to various embodiments, a sample quantity may be, for example, but not limited by, the number of cells or the concentration of a biomolecule. For each graph shown in FIG. 5, each point represents a serial dilution of an NTERA-2 cell sample taken for analysis. As previously mentioned, for various embodiments of methods for the analysis of PBA data, a proximity binding assay in which oligonucleotide-labeled BRP, as shown in FIG. 2, is a monoclonal or polyclonal antibody may be used. The exemplary PBA data shown was generated with an embodiment of a proximity binding assay utilizing an antibody-based BRP and qPCR analysis using TaqMan® PCR reagents In various embodiments of methods for the analysis of PBA data, as indicated in step 40 of method 100 of FIG. 1, the average Ct value for the non-protein control (NPC) samples or background samples associated with a particular set of samples may be subtracted from the average Ct values for each data point in the dilution series for each sample. An example of the background corrected Ct (bcCt) values for each data point for each curve for the OCT3/4 protein in the NTERA-2 cells is shown in FIG. 6. As one of ordinary skill in the art of oligonucleotide analysis by PCR is apprised, the graphs for the data presented are normally of parallel orientation for the linear phase of an amplification reaction. As can be clearly seen in FIG. 6, the PBA data for this exemplary analysis of OCT3/4 in NTERA cells is atypical of such amplification data. In that regard, various embodiments of analysis of PBA data specifically address the atypical nature of data generated for such analyses.

According to various embodiments of methods for the analysis of PBA data, as indicated in step 50 of method 100 of FIG. 1, the linear range of the relationship between the background corrected Ct (bcCt) values and the sample quantity, for example, but not limited by, the number of cells or the concentration of a biomolecule, may then be determined. Various embodiments of methods for the analysis of PBA data may be described by the following formula:

$$\frac{\rho_{p,s2}}{\rho_{p,s1}} = b^{[(\hat{B}_{s2} - bcCt_{th}/\hat{A}_{s2}) - (\hat{B}_{s1} - bcCt_{th}/\hat{A}_{s1})]} \quad \text{Eq. 1}$$

Where:

$$\frac{\rho_{p,s2}}{\rho_{p,s1}} = \text{Concentration,}$$

ρ, of a protein, p, in samples, s2 and s1:
b=base of the exponential increase in signal amplification
Âs, B̂s=The slope and intercept of linear portion of a plot of bcCt v. $\log_{10} Q_s$ and
$bcCt_{th}$=a bcCt value calculated from a selected threshold for a plot of bcCt v. $\log_{10} Q_s$.

As will be discussed in more detail subsequently, a simplified expression may be given as:

$$\frac{\rho_{p,s2}}{\rho_{p,s1}} = b^{[(X_1 - X_2)]} \quad \text{Eq. 2}$$

Figure 7:
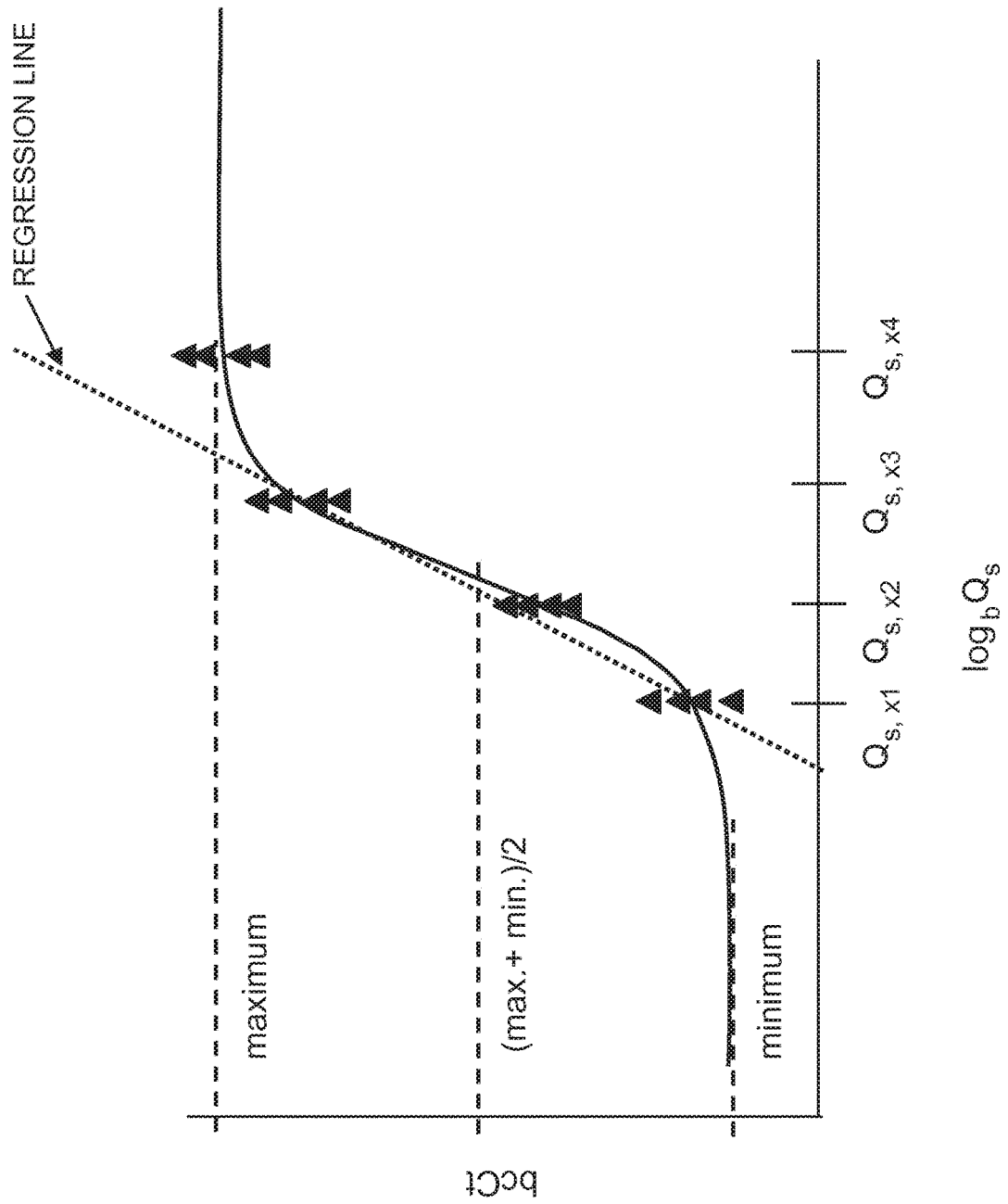
FIG. 7 depicts various embodiments of a method for the determination of a linear range of a graph.

Where:

$$\frac{\rho_{p,s2}}{\rho_{p,s1}} = \text{Concentration,}$$

ρ, of a protein, p, in samples, s2 and s1;
b=base of the exponential increase in signal amplification
s1=is a reference sample
s2=is a test sample
$X_1$=is the input quantity at which the regression line of the reference sample intersects the selected threshold
$X_2$=is the input quantity at which the regression line of the test sample intersects the selected threshold For various embodiments of step 50 of method 100 of FIG. 1, the linear range may be determined as depicted in FIG. 7. In FIG. 7, depicts a sigmoidally shaped curve, representing an idealized behavior for various embodiments of PBA data. Various data points for the log of the input quantity of a sample $Q_s$, such as the number of cells or the concentration of a protein in sample are shown in FIG. 7, in which replicates for each point, $Q_{s,x}$ are indicated by the dark triangles. Each point, $Q_{s,x}$, then, is an average of the replicates shown. In various embodiments of step 50 of method 100, a maximum and minimum value for bcCt for a sigmoidal curve may be determined, as depicted in FIG. 7. In various embodiments, second derivative data may be used to determine a maximum and minimum point. For various embodiments, a maximum and minimum bcCt values may be obtained through extrapolation, and shown in FIG. 7. In various embodiments, after such values have been obtained, a point on the curve at a bcCt value half way in between the maximum and minimum values of bcCt may be determined. For various embodiments of step 50 of method 100, a data point close to a half way point on the curve may be selected. In the example shown in FIG. 7, $Q_{s,x2}$ is a point close to the half way point on the curve. According to various embodiments of step 50 of method 100, once a data point from the data set has been selected, at least one additional near-neighbor data point is selected, and a linear fit to the group of points selected may be done using any of a variety of linear regression algorithms. For example, in some embodiments of step 50 of method 100, in addition to a selected point, such as $Q_{s,x2}$, a single point, such as either of $Q_{s,x1}$ and $Q_{s,x3}$ may be selected. According to various embodiments of step 50 of method 100, in addition to a selected point, such as $Q_{s,x2}$, multiple points, such as $Q_{s,x1}$ and $Q_{s,x3}$ may be selected.

In various embodiments of step 50 of method 100 of FIG. 1, the process may iterate to include additional points. According to various embodiments of step 60 of method 100, an evaluation of goodness of fit may be done for every iteration of linear regression performed. In some embodiments, a calculated correlation coefficient may be used to assess whether or not the selection of points is a good fit to a straight line. In various embodiments of step 50 of method 100, a goodness of fit may be determined by the a priori evaluation of whether or not a new point would be a to a line. For such embodiments, the difference between the bcCt value for a data point and a bcCt value extrapolated to a line determined by regression analysis from that point may be determined, and a difference falling within the spread of the data points for that point may constitute an acceptable goodness of fit. For example, in FIG. 7, for the data point $Q_{s,\,x4}$, the difference between the bcCt value for that point on the graph, and for a bcCt value at that data point on the regression line is clearly out side of the spread of all the replicates for that point. For various embodiments of step 50 of method 100, point at $Q_{s,\,x4}$ would not be included as an additional point.

Figure 8:
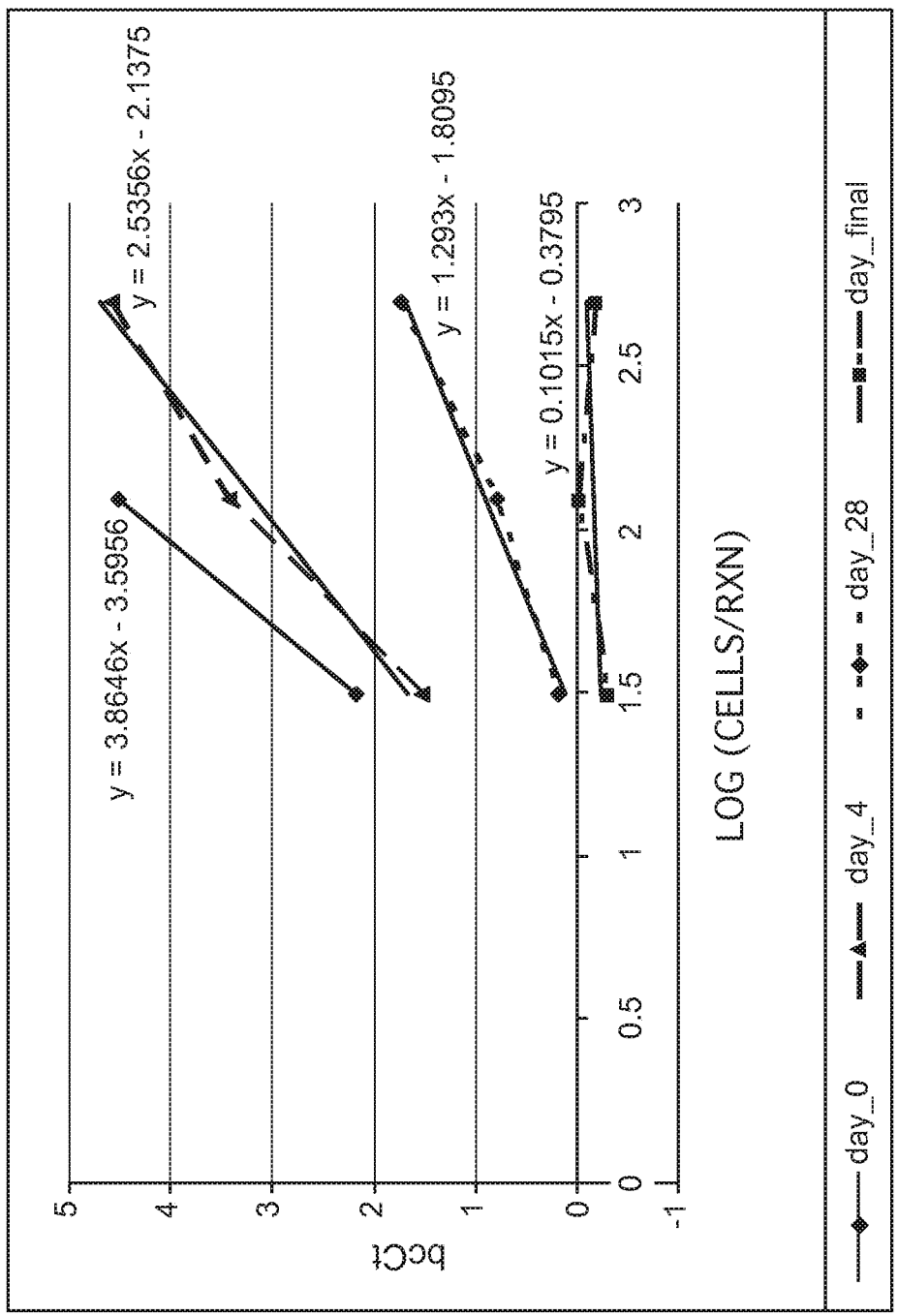
FIG. 8 depicts the exemplary graphs of FIG. 6 for which the linear ranges of the graphs have been determined.

In FIG. 8, for various embodiments of step 50 of method 100 of FIG. 1, the determination of the linear range is depicted for the exemplary determination of OCT3/4 in NTERA-2 cell samples. As previously discussed, it is clear from the inspection of the slopes of the lines in FIG. 8, that there is a significant deviation from a parallel orientation for these lines.

Figure 9:
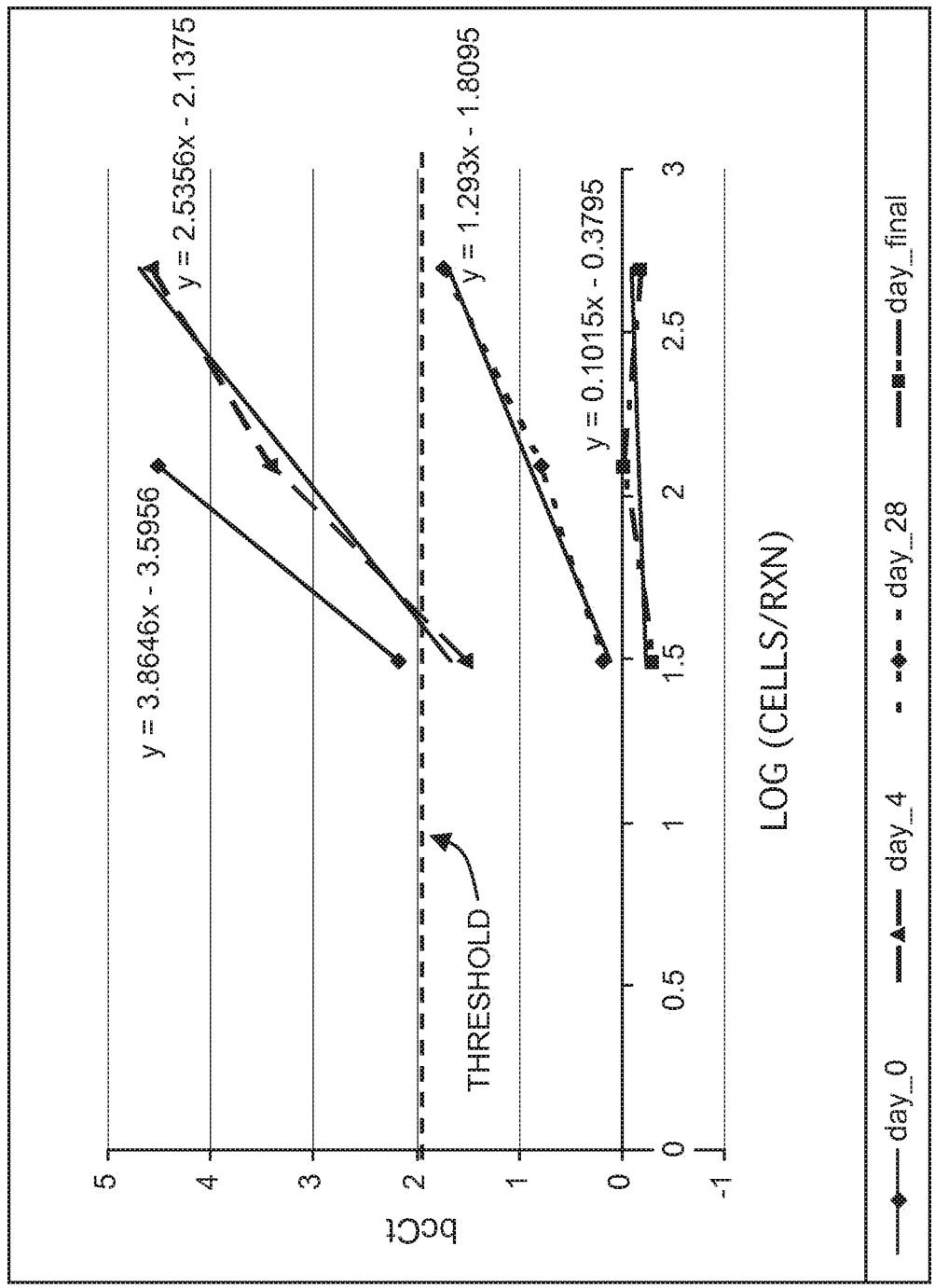
FIG. 9 depicts the exemplary graphs of FIG. 8 in which a threshold value has been selected.

For various embodiments of methods for the analysis of PBA data, as indicated in step 60 of method 100 of FIG. 1, a threshold value for bcCt may be selected. In various embodiments of step 60 of method 100, a threshold value may be selected based on the noise or variation in the data. According to various embodiments, a factor between about 1.0 to about 5.0 times Ct may be selected, as for various proximity binding assays the noise is in the range of about 0.5 to about 1.5 times Ct. For various embodiments of method 100 of FIG. 1, a threshold of between about 0.5 bcCt to about 2.5 bcCt may be selected. According to various embodiments, a user may select a value for threshold. In FIG. 9, for various embodiments of step 60 of method 100 of FIG. 1, the selection of a threshold value of 2.0 bcCt is depicted for the exemplary determination of OCT3/4 in NTERA-2 cell samples.

Figure 10:
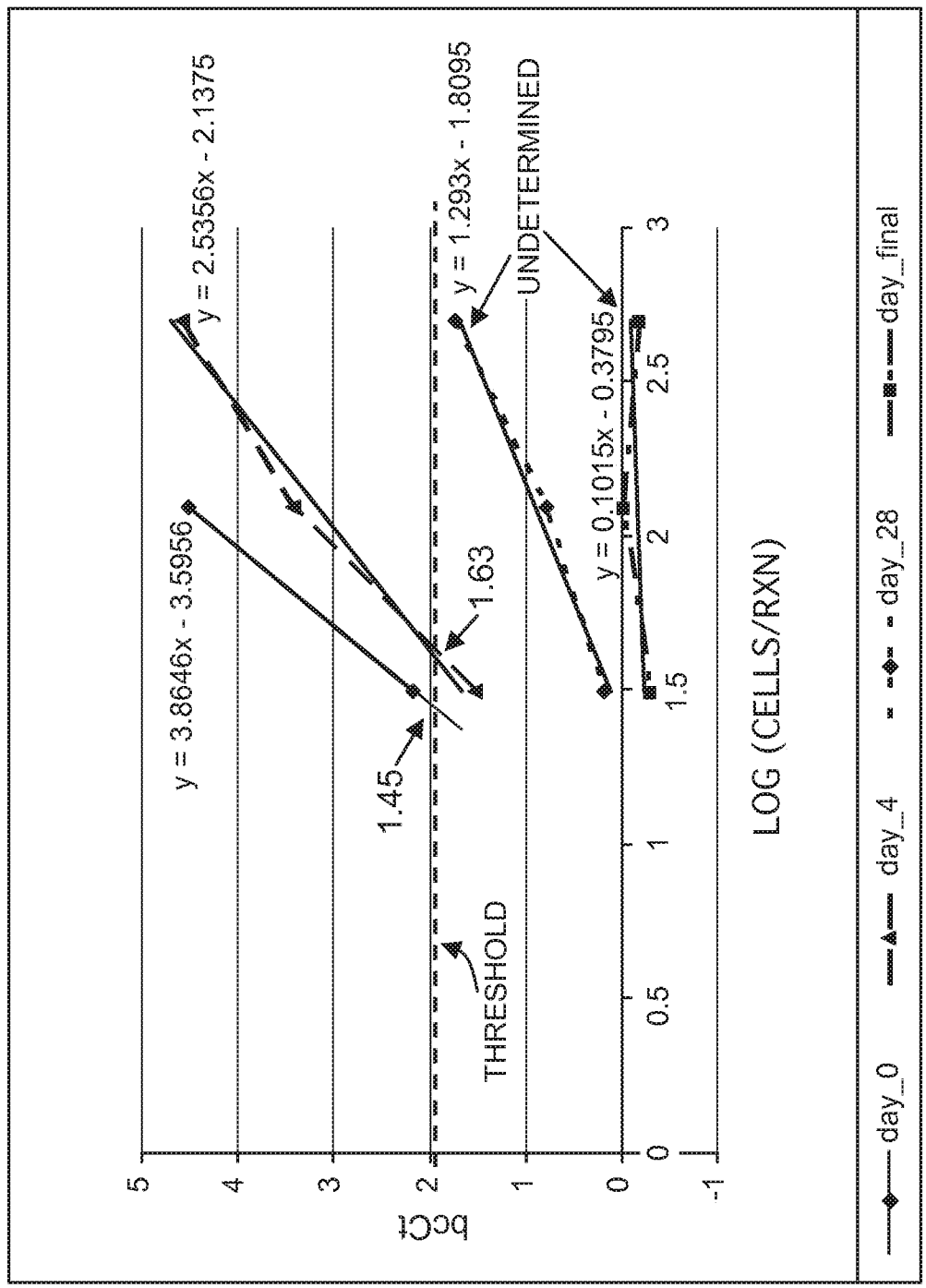
FIG. 10 depicts the exemplary graphs of FIG. 9 indicating the x value where y is the threshold value.

After the selection of a threshold value, for various embodiments of step 70 of method 100 of FIG. 1, an x value at which the linear portion of PBA data reaches the threshold may be determined. For example, in FIG. 10, the determination of the x values are depicted for an exemplary determination of OCT3/4 in NTERA-2 cell samples, according to various embodiments of a determination of a sample quantity. In FIG. 10, a value of the x value may for be determined for OCT3/4 in NTERA-2 day 0 and day 4 cell samples. For various embodiments of method 100 of FIG. 1, the extrapolation of the linear portion of the bcCt versus $\log_{10}$, of sample quantity may be done to determine a value of sample quantity. For example, in FIG. 10, a $\log_{10}$, value of 1.45 for OCT3/4 in the day 0 sample and a $\log_{10}$ value of 1.63 for the OCT3/4 in the day 4 sample may be determined through extrapolation. From these logarithmic values, a relative quantitation, or the ratio of the day 4 to the day 0 values of 28.18 and 42.65, respectively, yields a relative quantitation (RQ) value of 0.66. It is clear from these data that OCT3/4 was downregulated in the day 4 sample. Finally, as day 28, and the final day have such low levels of OCT3/4, an x-intercept value cannot be determined for these samples, and they are marked as shown in FIG. 10. These data are displayed graphically in FIG. 11.

Alternatively, according to various embodiments of step 70 of method 100 of FIG. 1, a relative quantitation of the day 4 to the day 0 sample may be calculated directly using Eq. 1. For example, by substituting all the values from the linear regression analysis given for day 4 and day 0, as well as a $bcCt_{th}$ value of 2 into Eq. 1, an RQ value of $1^{-0.18}$ is obtained, which is a value of the ratio of the concentrations for OCT3/4, or RQ, of 0.66. According to various embodiments of step 70 of method 100 of FIG. 1, sample quantity may be, for example, but not limited by, the number of cells in a sample, or the concentration of a biomolecules, such as a protein.

Figure 12:
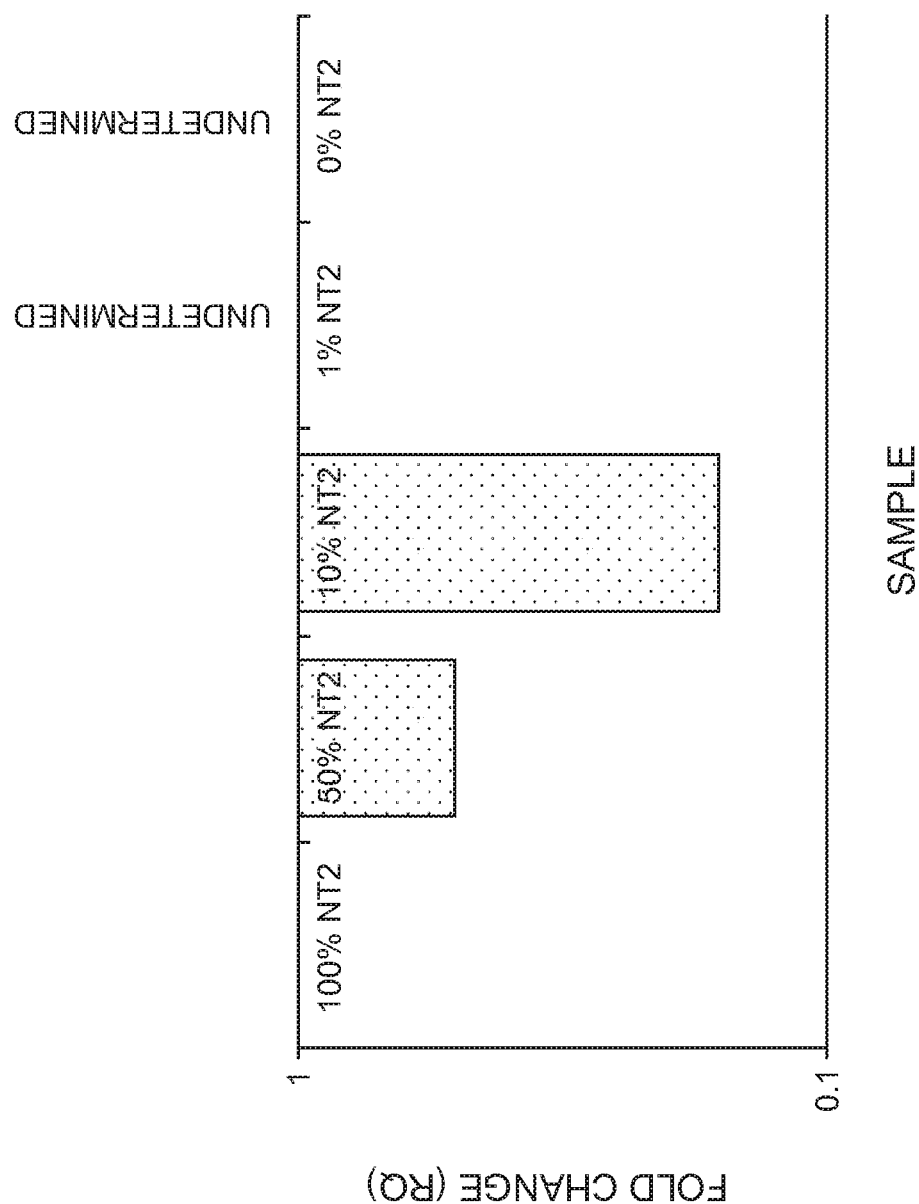
FIG. 12 depicts a presentation of data for the exemplary proximity binding assay of FIG. 5 according to various embodiments of methods for the analysis of PBA data.

In FIG. 12, the results of a validation study for the determination of the OCT3/4 target protein in the NTERA-2 cells is shown, according to various embodiments of a method for the analysis of PBA data. In this validation study, the NTERA-2 cell lysate was spiked in with a Raji cell lysate, as shown in the table below:

TABLE 1

| Sample | Sample Composition | | Relative Quantitation | |
|---|---|---|---|---|
| | NTERA2 lysate | Raji Lysate | Expected | Result |
| Test__50% | 50% | 50% | 0.5 | 0.52 |
| Test__10% | 10% | 90% | 0.1 | 0.12 |

For this study, a series of dilution were done as indicated in FIG. 12. PBA data was collected over a period of days on different instruments, so that the data analyzed include within day, day-to-day, as well as instrument-to-instrument noise. As previously mentioned, one of ordinary skill in the art of various bioanalyses using antigen-binding recognizes that such bioanalyses may be impacted by matrix effects. In that regard, spiking the NTERA-2 cell lysate with the Raji cell lysate presents a validation study in which quantitative recovery may be impacted by matrix effects, as well as cross-reactivity, due to the presence of proteins from the Raji cell lysate in the assay mixture. For the validation study presented in FIG. 12, as can be seen by the inspection of Table 1, the results for the various dilutions validated the data analysis method for determining the expected results, reporting an RQ of 52% for the 50% dilution sample, 12% for the 10% dilution sample, and "undetermined" for the unspiked control. As the 1% dilution was additionally below the limit of detection for the assay, it was also reported as "undetermined".

Figure 13:
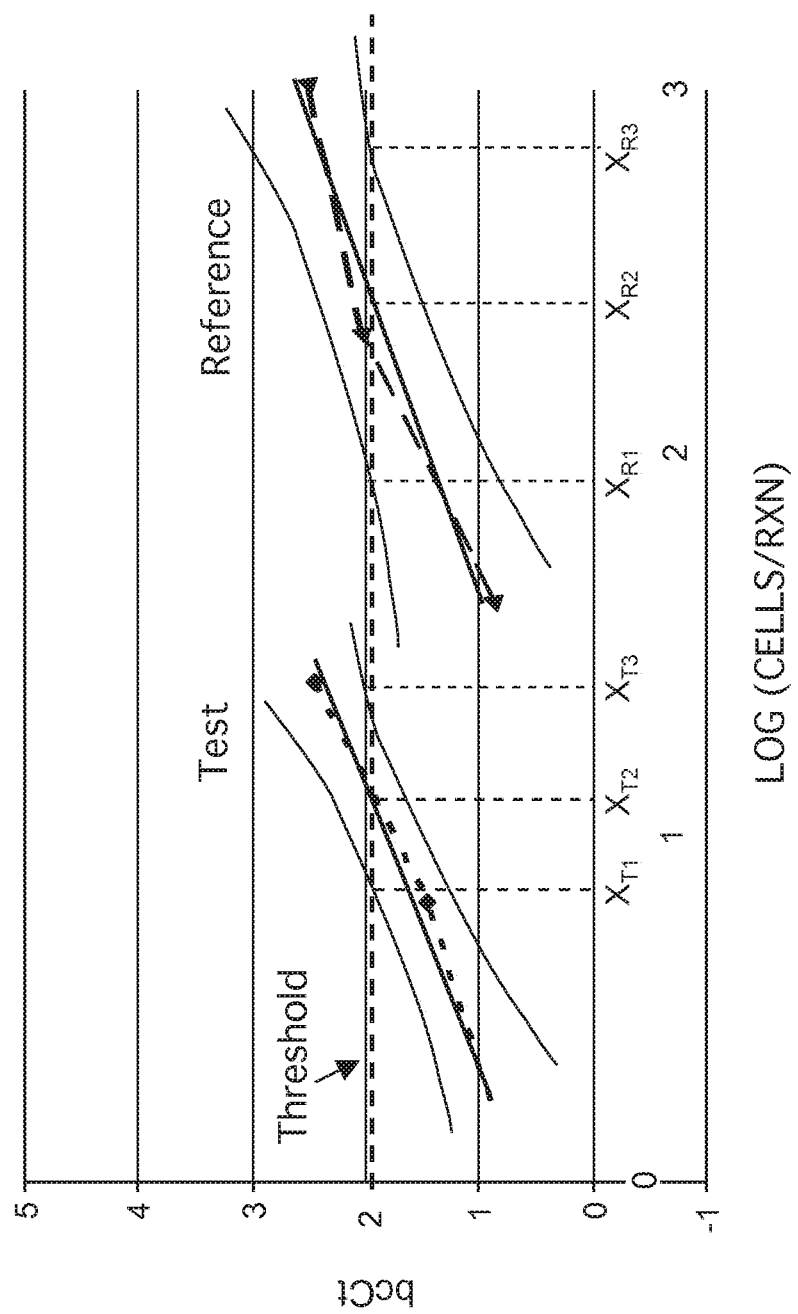
FIG. 13 is in reference to the determination of a confidence interval for a sample quantity as determined according to various methods for the analysis of PBA data.

According to various embodiments of method 100 of FIG. 1, a confidence value may be generated for the sample quantity determined in step 70. For various embodiments, a confidence value for a sample quantity may be derived from confidence bands constructed about the lines determined using linear regression, as depicted in FIG. 13.

For example, under an assumption of the normal distribution of the data, a confidence band about a regression line for the linear portion of a curve given by Eq. 1 may be given by:

$$C_a(x) = \hat{A}x + \hat{B} \pm \tilde{t}_{N-2,1-\alpha/2}\hat{\sigma}\sqrt{\frac{1}{N} + \frac{(x-\bar{x})^2}{\sum(x_i-\bar{x})^2}} \quad \text{Eq. 3}$$

$$\text{For } \tilde{t}_{N-2,1-\alpha/2}, \int_{-\infty}^{\tilde{t}_{N-2,1-\alpha/2}} t_{N-2} = 1 - \alpha/2$$

where $t_{N-2}$ is the t-distribution with N−2 degrees of freedom.

In reference to FIG. 13, and Eq. 2, the fold change for the comparison of the quantity of sample in the test versus the reference is given by:

$$\frac{\rho_{p,s2}}{\rho_{p,s1}} = b^{[(X_{R2}-X_{T2})]} \qquad \text{Eq. 4}$$

Where:

$$\frac{\rho_{p,s2}}{\rho_{p,s1}} = \text{Concentration},$$

ρ, of a protein, p, in samples, s2 and s1;
b=base of the exponential increase in signal amplification
s1=is a reference sample
s2=is a test sample
$x_{R2}$=is the input quantity at which the regression line of the reference sample intersects the selected threshold
$x_{T2}$=is the input quantity at which the regression line of the test sample intersects e selected threshold Then, for various embodiments of determining a confidence value according to various methods for the analysis of PBA data, a confidence as depicted in FIG. 13, a confidence interval for the test sample may be given as:

$$b^{[(\alpha R1 - xT3)]}, b^{[(\alpha R3 - xT1)]} \qquad \text{Eq. 5}$$

Figure 11:
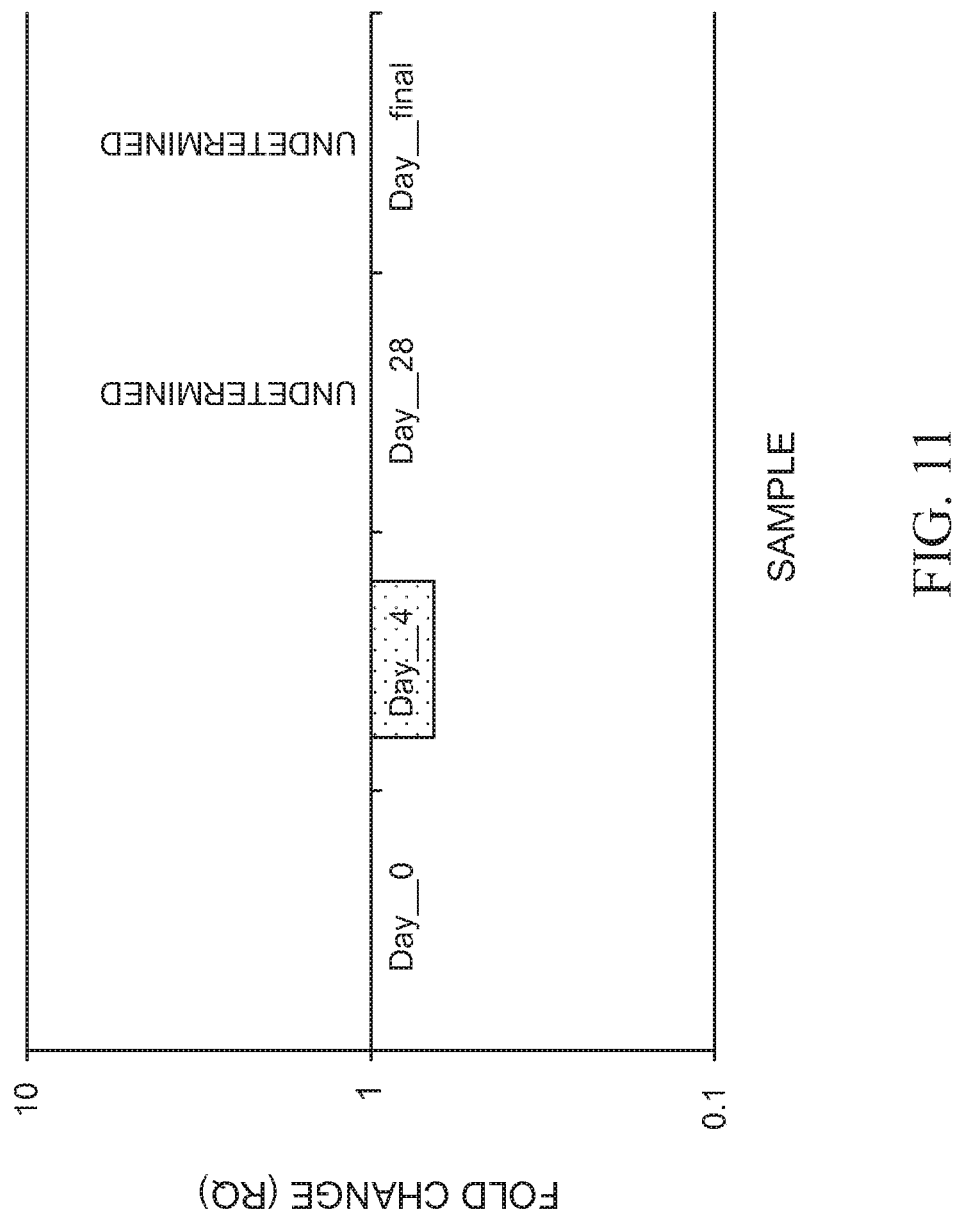
FIG. 11 depicts a validation study of the exemplary proximity binding assay of FIG. 5 according to various embodiments of a method for the analysis of PBA data.

Finally, according to various embodiments of methods for the analysis of PBA data, as shown in step 80 of method 100 of FIG. 1, the PBA data may be outputted to an user for making determinations of samples analyzed for, for example, but not limited by, the up or down regulation of a protein or proteins in a cell line, the concentration of a protein in a biological sample, the post-translational or synthetic modification of a protein. For various embodiments of methods of the analysis of PBA data, an output may be a graph, as shown in FIG. 11 and FIG. 12. As previously mentioned in the discussion of FIG. 8 and FIG. 4, various embodiments of a computer system may be utilized to implement various embodiments of step 80 of method 100 of FIG. 1 for the presentation of data outputted to a user for making determinations of samples using PBA data. Such embodiments of a computer system, as mentioned in the discussion of FIG. 8 and FIG. 4, may be utilized in the implementation of displaying, printing and otherwise conveying the presentation of PBA data to an end user. Accordingly, though the presentation of data in FIG. 11 and FIG. 12 is graphical, the presentation of PBA data may be in any useful format, for example, but not limited by, graphical, tabular, or narrative, and combinations thereof.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed is:

1. A method of using a proximity binding assay to determine the quantity of a target molecule in test samples, the method comprising:
    adding a first biorecognition probe modified with a first oligonucleotide sequence and a second biorecognition probe modified with a second oligonucleotide sequence to a first sample region comprising the test samples, a second sample region comprising reference samples, and a third sample region comprising negative control samples and lacking the target molecule, the first and second biorecognition probes being designed to readily attach to the target molecule, when present, and the first oligonucleotide sequence and the second oligonucleotide sequence being designed to readily bind when in proximity to each other, resulting in a target for amplification;
    obtaining, from the first sample region, the second sample region, and the third sample region, any targets for amplification resulting from adding;
    respectively combining any targets for amplification obtained from the first sample region, the second sample region, and the third sample region with labeling probes;
    conducting thermal cycling on respective combinations comprising the targets for amplification and the labeling probes;
    obtaining proximity binding assay data from detecting the labeling probes during or after thermal cycling, the proximity binding assay data comprising test sample data, reference sample data and negative control sample data; and
    processing the proximity binding assay data to determine a quantity of the target molecule in each of the test samples, wherein processing comprises using the negative control sample data to correct for background binding of the first oligonucleotide sequence and the second oligonucleotide sequence that occurs even without presence of the target molecule in a sample.

2. The method of claim 1 wherein processing the proximity binding assay data comprises:
    determining cycle threshold (Ct) values for the test sample data and the reference sample data;
    calculating background corrected Ct values for each value in the test sample data and the reference sample data using a corresponding value in the negative control sample data;
    determining a linear range for the background corrected Ct values as a function of sample quantity for the test sample data and the reference sample data;
    selecting a background corrected Ct value as a threshold value; and
    calculating a quantity for a target molecule in the test samples using the background corrected Ct threshold value, wherein the quantity is calculated by comparing a first sample quantity at the threshold value for the test sample data and a second sample quantity at the threshold value for the reference sample data to determine the quantity of a target molecule in the test samples.

3. The method of claim 1, further comprising determining a confidence value for the quantity determined for the target molecule in a test sample.

4. The method of claim 1, where the quantity determined for the target molecule in a test sample is relative.

5. The method of claim 1, where the quantity determined for the target molecule in a test sample is quantitative.

6. The method of claim 1, where the target molecule comprises a protein.

7. The method of claim 1, where the test samples comprise cell samples.

8. A kit for determining the quantity of a target molecule in a test samples, the kit comprising:
   a plurality of first biorecognition probes and a plurality of second biorecognition probes, a first biorecognition probe of the plurality of first biorecognition probes being modified with a first oligonucleotide sequence and a second biorecognition probe of the plurality of second biorecognition probes being modified with a second oligonucleotide sequence, the first biorecognition probe and the second biorecognition probe being designed to readily attach to the target molecule, when present, and the first oligonucleotide sequence and the second oligonucleotide sequence being designed to readily bind when in proximity to each other, resulting in a target for amplification; and
   a computer program product embedded in a non-transitory computer readable medium comprising executable instruction code that, when executed by one or more processors causes the one or more processors to perform processing comprising:
      processing proximity binding assay data to determine a quantity of the target molecule in the test samples; wherein:
         the proximity binding assay data comprises test sample data, reference sample data, and negative control sample data;
         the test sample data has been obtained by detecting labeling probes during or after thermocycling of a combination comprising the labeling probes and any obtained targets for amplification, the obtained targets for amplification having been obtained from adding the first and second biorecognition probes to the test samples;
         the reference sample data has been obtained by detecting labeling probes during or after thermocycling of a combination comprising the labeling probes and any obtained targets for amplification, the obtained targets for amplification having been obtained from adding the first and second bio recognition probes to reference samples;
         the negative control sample data has been obtained by detecting labeling probes during or after thermocycling of a combination comprising the labeling probes and any obtained targets for amplification, the obtained targets for amplification having been obtained from adding the first and second bio recognition probes to negative control samples in which the target molecule is not present; and
      processing proximity binding assay data comprises using the negative control sample data to correct for background binding of the first oligonucleotide sequence and the second oligonucleotide sequence that occurs even without presence of the target molecule in a sample.

9. The kit of claim 8 wherein processing the proximity binding assay data comprises:
   determining cycle threshold (Ct) values for the test sample data and the reference sample data;
   calculating background corrected Ct values for each value in the test sample data and the reference sample data using a corresponding value in the negative control sample data;
   determining a linear range for the background corrected Ct values as a function of sample quantity for the test sample data and the reference sample data;
   selecting a background corrected Ct value as a threshold value; and
   calculating a quantity for a target molecule in the test samples using the background corrected Ct threshold value, wherein the quantity is calculated by comparing a first sample quantity at the threshold value for the test sample data and a second sample quantity at the threshold value for the reference sample data to determine the quantity of a target molecule in the test samples.

10. The kit of claim 8, wherein the executable instruction code, when executed by the one or more processors causes the one or more processors to perform processing further comprising determining a confidence value for the quantity determined for the target molecule in a test sample.

11. The kit of claim 8, where the quantity determined for the target molecule in a test sample is relative.

12. The kit of claim 8, where the quantity determined for the target molecule is quantitative.

13. The kit of claim 8, where the target molecule comprises a protein.

14. The kit of claim 8, where the test samples comprise cell samples.

* * * * *